(12) United States Patent
Jensen

(10) Patent No.: US 9,370,537 B2
(45) Date of Patent: Jun. 21, 2016

(54) COMPOSITIONS AND METHODS FOR REDUCING INFLAMMATION

(75) Inventor: Gitte S. Jensen, Klamath Falls, OR (US)

(73) Assignee: Cerule, LLC, Klamath Falls, OR (US)

( * ) Notice: Subject to any disclaimer, the term of this patent is extended or adjusted under 35 U.S.C. 154(b) by 1076 days.

(21) Appl. No.: 13/259,405

(22) PCT Filed: Apr. 2, 2010

(86) PCT No.: PCT/US2010/029847
§ 371 (c)(1),
(2), (4) Date: Sep. 23, 2011

(87) PCT Pub. No.: WO2010/115149
PCT Pub. Date: Oct. 7, 2010

(65) Prior Publication Data
US 2012/0014986 A1    Jan. 19, 2012

Related U.S. Application Data

(60) Provisional application No. 61/166,653, filed on Apr. 3, 2009.

(51) Int. Cl.
*A61K 35/748* (2015.01)
*A61K 35/74* (2015.01)

(52) U.S. Cl.
CPC ............. *A61K 35/74* (2013.01); *A61K 35/748* (2013.01)

(58) Field of Classification Search
None
See application file for complete search history.

(56) References Cited

U.S. PATENT DOCUMENTS 6,814,961 B1 * 11/2004 Jensen et al. .................. 424/93.1
7,651,690 B2 * 1/2010 Jensen et al. ............. 424/195.17
2006/0233737 A1    10/2006 Janailhac et al.
2007/0003647 A1    1/2007 Jensen et al.
2007/0037776 A1 * 2/2007 Richardson ............ A61K 9/007
                                                                514/54

FOREIGN PATENT DOCUMENTS

WO    WO 2008/000431    1/2008

OTHER PUBLICATIONS

Arnon et al., Photochemical Activity and Components of Membrane Preparations from Blue-Green Algae, 1974, Biochimica et Biophysica Acta, 357: 231-245.*
Hart et al., "Natural Killer Cell Activation and Modulation of Chemokine Receptor Profile In Vitro by an Extract From the Cyanophyta Aphanizomenon Flos-aquae," *J. Med. Food*, 10(3): 435-441, 2007.
Jensen et al., "An antiinflammatory immunogen from yeast culture induces activation and alters chemokine receptor expression on human natural killer cells and B lymphocytes in vitro", *ScienceDirect, Nutrition Research* 27:327-335, 2007.
Jensen et al., "In vitro and in vivo antioxidant and anti-inflammatory capacities of an antioxidant-rich fruit and berry juice blend. Results of a pilot and randomized, double-blinded, placebo-controlled, crossover study", *J. Agric. Food Chem.*, 56:8326-8333, 2008.

* cited by examiner

*Primary Examiner* — Terry A McKelvey
*Assistant Examiner* — Catheryne Chen
(74) *Attorney, Agent, or Firm* — Klarquist Sparkman, LLP

(57) ABSTRACT

Blue-green algae, such as *Aphanizomenon flos aquae* (AFA) or *Spirulina* (*Arthrospira*) can be fractionated. Anti-inflammatory aqueous fractions of blue-green algae are described herein that include low molecular weight molecules. Methods for reducing inflammation in a subject are also described. These methods include administering to the subject compositions comprising a therapeutically effective amount of the anti-inflammatory aqueous fraction blue-green algae, or dried form thereof, thereby reducing inflammation.

16 Claims, 5 Drawing Sheets

COMPOSITIONS AND METHODS FOR REDUCING INFLAMMATION

CROSS REFERENCE TO RELATED APPLICATION

This is the U.S. National Stage of International Application No. PCT/US2010/029847, filed Apr. 2, 2010, which was published in English under PCT Article 21(2), which in turn claims the benefit of U.S. Provisional Application No. 61/166,653, filed on Apr. 3, 2009,which is incorporated by reference herein in its entirety.

FIELD

This application relates to methods of reducing inflammation in animal and human cells, tissue, and organisms, and specifically to the use of an aqueous extract of blue-green algae that mainly includes molecules with a molecular weight of less than about 100 kDa and which is substantially free of phycocyanin to reduce inflammation.

BACKGROUND

Inflammation is the complex biological response of vascular tissues to harmful stimuli, such as pathogens, damaged cells, or irritants. It is a protective attempt by the organism to remove the injurious stimuli as well as initiate the healing process for the tissue.

Humans and many animals are afflicted with a variety of inflammatory disorders, including allergy, asthma, atherosclerosis, dermatitis (such as allergic chronic contact dermatitis and environmental chronic contact dermatitis), laminitis, reactive airway diseases and processes (such chronic obstructive pulmonary disease ("COPD"), inflammatory airway disease ("IAD"), inflammatory bowel disease, and rheumatoid arthritis, ulcerative colitis, Crohn's disease, stroke-induced brain cell death, ankylosing spondylitis, fibromyalgia. Autoimmune diseases such as asthma, multiple sclerosis, systemic lupus erythematosus, scleroderma, systemic sclerosis, and Sjögren's syndrome are inflammatory disorders characterized by dysregulation of the immune system and inappropriate mobilization of body's defenses against its own healthy tissue.

Analgesics, anti-inflammatory agents, (both steroidal and non-steroidal), and immunosuppressive agents are used to attempt to manage these disorders. However, a need remains for additional agents to treat inflammation and inflammatory disorders.

SUMMARY

Blue-green algae, such as *Aphanizomenon flos aquae* (AFA) or *Spirulina* (*Arthrospira*) can be fractionated. Compositions that include anti-inflammatory aqueous fractions of blue-green algae, and which are substantially free of phycocyanin, are described herein. In some embodiments, the isolated fraction has a molecular weight distribution wherein at least 95% of the molecules in the isolated fraction are less than a cut-off weight and the cut-off weight is not more than about 100 kDa or less. The cut-off weight in the fraction can vary. Thus, in other embodiments, these fractions include molecules of less than about 100 kDa, and not about 100 kDa or greater; less than about 50 kDa, and not about 50 kDa or greater; less than about 10 kDa, and not about 10 kDa or greater; or less than about 5 kDa, and not about 5 kDa or greater. Generally, the fractions are substantially free of phycocyanin, and thus contain less than about 5 mg/L of the protein phycocyanin. These fractions are anti-inflammatory, and can be used to reduce inflammation. In some embodiments, the fractions inhibit lipoxygenase activity.

Methods for reducing inflammation in a subject are provided herein. These methods include administering to the subject a therapeutically effective amount of a composition comprising the anti-inflammatory aqueous fraction of blue-green algae, thereby reducing inflammation. In some embodiments, the subject has an inflammatory disorder.

Additionally provided are anti-inflammatory fractions of *Aphanizomenon flos aquae* or species of *Spirulina* (*Arthrospira*), wherein the anti-inflammatory fractions have a molecular weight distribution wherein at least 95% of the molecules in the anti-inflammatory fractions are less than a cut-off weight and the cut-off weight is not more than about 100 kDa or less. The fractions are produced by extracting *Aphanizomenon flos aquae* or a species of *Spirulina* (*Arthrospira*) in water or a buffered salt solution to produce an extract; and isolating molecules from the extract of less than a cut-off weight of not more than about 100 kDa or less. The cut-off weight in the fractions can vary. Thus, in other embodiments, these fractions include molecules less than about 100 kDa, and not 100 kDa or greater; less than about 50 kDa, and not 50 kDa or greater; less than about 10 kDa, and not 10 kDa or greater; or less than about 5 kDa, and not 5 kDa or greater. Such extracts are substantially free of phycocyanin and thus contain less than 5 mg/L of phycocyanin.

The foregoing and other features and advantages will become more apparent from the following detailed description of several embodiments, which proceeds with reference to the accompanying figures.

DETAILED DESCRIPTION

Figure 1:
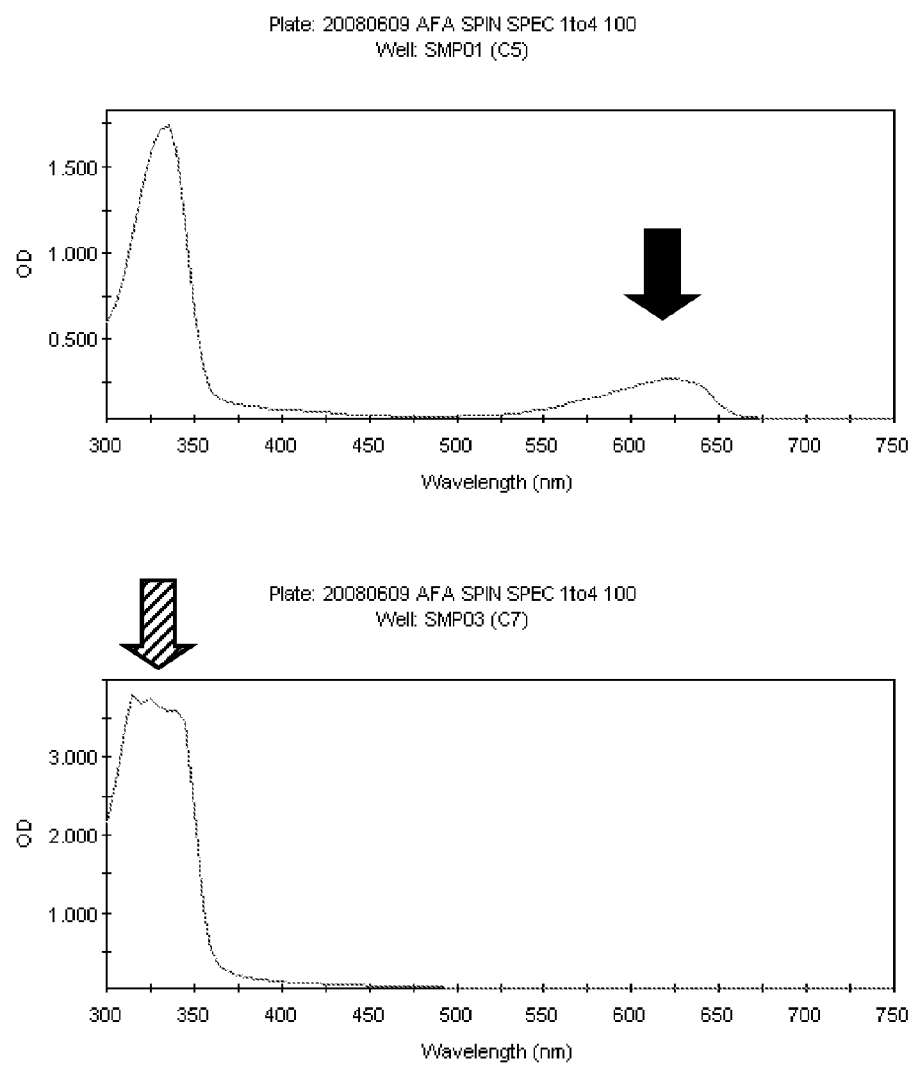
FIG. 1 is a graph illustrating the spectral scan of light absorbance from 400 to 700 nm of crude water extract from *Aphanizomenon flos-aquae* (AFA) (top), and the 1117 fraction (bottom). The peak at 620 nm reflects the presence of Phycocyanin, and is only seen in the crude extract, not in the 1117 fraction.

Blue-green algae, such as *Aphanizomenon flos aquae* (AFA) or *Spirulina* (*Arthrospira*) can be fractionated. Disclosed herein are anti-inflammatory fractions of blue-green algae. Methods are also disclosed for treating inflammation.

I. Abbreviations

AFA: *Aphanizomenon flos aquae*
ADV: acoustic doppler velocimeter
ANOVA: analysis of variance
ARDS: acute respiratory distress syndrome
COPD: chronic obstructive pulmonary disease
COX: cyclooxygenase DCF-DA: dichlorodihydrofluorescein diacetate
f-MLP: formyl-Met-Leu-Phe
FEV1: forced expired volume in one second
FEF: forced expiratory flow
FVC: forced vital capacity
g: gram
HPLC: high performance liquid chromatography
IAD: inflammatory airway disease
IFN: interferon
Ig: immunoglobulin
IL: interleukin
IV: intravenous
IP: intraperitoneal
kg: kilogram
LDV: laser doppler velocimeter
LTB4: Leukotriene B4
MS: mass spectrometry
NK: natural killer
NSAID: non-steroidal anti-inflammatory drug
PBMC: peripheral blood mononuclear cells
PBS: phosphate buffered saline
PMN: polymorphonuclear
PTGS: prostaglandin-endoperoxide synthase
RA: Rheumatoid Arthritis
ROS: reactive oxygen species
TLC: thin layer chromatography
TNF: tumor necrosis factor
UV-VIS: ultra-violet visible
VLC: vacuum liquid chromatography II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: Providing blue-green algae to a subject includes administering whole blue-green algae cells or extracts of blue-green algae cells. Routes of administration include, but are not limited to, oral and parenteral routes, such as intravenous (IV), intraperitoneal (IP), rectal, topical, ophthalmic, nasal, and transdermal. Oral administration includes both whole blue-green algae and extracts of blue-green algae. If administered orally, the whole cells or extracts may be provided or administered in the form of a unit dose in solid, semi-solid, or liquid dosage form such as tablets, pills, powders, liquid solutions, or liquid suspensions. However, extracts of blue-green algae also may be administered intravenously in any conventional medium for intravenous injection, such as an aqueous saline medium, or in a blood plasma medium. The medium also may contain conventional pharmaceutical adjunct materials, such as pharmaceutically acceptable salts to adjust the osmotic pressure, lipid carriers (e.g., cyclodextrins), proteins (e.g., serum albumin), hydrophilic agents (e.g., methyl cellulose), detergents, buffers, preservatives, and the like. A more complete explanation of acceptable pharmaceutical carriers can be found in *Remington: The Science and Practice of Pharmacy* (19$^{th}$ Edition, 1995) in chapter 95.

Allergy: A collection of symptoms caused by an exaggerated immune response or reaction to substances that do not trigger an immune response in most people, and thus is an example of an immune-mediated disorder. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions which could be provoked by many antigens. In practice, these types do not necessarily occur in isolation from each other.

Allergens cause the production of immunoglobulin E (IgE), an antibody that all of us have in small amounts. Allergic persons, however, produce IgE in abnormally quantities. During the sensitization period in allergy, IgE is overproduced. Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains, or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms.

Asthma: Bronchial asthma is a complex clinical syndrome characterized by reversible airway obstruction, bronchial hypersensitiveness, edema in airway and eosinophilic-lymphocytic inflammation. Clinically, bronchial asthma accompanies such symptoms as spasmodic dyspnea, coughing, wheezing, etc. These symptoms occur intermittently with periods of acute aggravation and silence interposed Blue-Green Algae: Gram-negative photosynthetic bacteria belonging to Division Cyanophyta that may exist in unicellular, colonial, or filamentous forms. Representative blue-green algae include, but are not limited to, *Spirulina* (*Arthrospira*) species and *Aphanizomenon* species. *Aphanizomenon flos aquae* (AFA) is one specific, non-limiting type of blue-green algae.

The term "algae" is the plural form of "alga," which is a cell of a microalgae species. For example (and without limitation), "blue-green algae" refers to multiple cells of a single *Aphanizomenon* species, multiple cells of a single *Spirulina* (*Arthrospira*) species, or a mixture of cells from multiple *Aphanizomenon* and/or *Spirulina* (*Arthrospira*) species.

Circulatory System: In animals, the circulatory system is composed of the structures that move blood and blood components throughout the body, including the vascular and lymph systems. The components of the circulatory system include the heart, blood vessels (arteries, veins, and capillaries), and lymph vessels.

Component of Blue-Green Algae: Any fraction, extract, or isolated or purified molecule from a blue-green algae cell. In one embodiment, the component (or molecule) is a protein or a glycoprotein or nucleic acid. In another embodiment, the component (or molecule) is a phytochemical. Thus, the blue-green algae are disrupted, an inorganic or organic solvent is added, and components (or molecules) are collected. Specific, non-limiting examples of components are isolated using high performance liquid chromatography, thin layer chromatography, affinity column, magnetic beads or distillation. In one embodiment, fractionation to isolate components or molecules is based on the molecular weight or the hydrophobicity of the molecules of the blue-green algae. For example, the fraction can include those molecules of less than about 50 kDa, and not 50 kDa or greater; less than about 10 kDa, and not 10 kDa or greater; or less than about 5 kDa, and not 5 kDa or greater.

Cut-off Weight: A molecular weight cut-off indicates the exclusion of molecules in a composition above a specified molecular weight. The exclusion of molecules above a particular cut-off weight can be achieved by any method known to the art of separating molecules, including, but not limited to ultrafiltration and chromatography, and will produce a composition that has a specific molecular weight distribution. In some examples, this can be achieved by use of ultrafiltration filters with a defined molecular weight cut-off, such as 100 kDa, 50 kDa, 30 kDa, 10 kDa, 5 kDa or 3 kDa. In other examples, separation of molecules according to a specified cut-off weight can be achieved by chromatographic methods, such as size exclusion chromatography.

Cyclooxygenase (Cox): An enzyme protein complex present in most tissues that catalyses two steps in prostaglandin biosynthesis and produces prostaglandins and thromboxanes from arachidonic acid. Cox-2 is also known as prostaglandin-endoperoxide synthase (PTGS), and is a key enzyme in prostaglandin biosynthesis. The cyclooxygenase activity converts arachidonate and $2O_2$ to prostaglandin $G_2$; the hydroperoxidase activity uses glutathione to convert prostaglandin $G_2$ to prostaglandin $H_2$. Cyclooxygenase activity is inhibited by aspirin like drugs, accounting for their anti-inflammatory effects. Cyclooxygenase (Cox) exists as two isozymes, Cox-1 and Cox-2. Cox-2, but not Cox-1, is an inducible enzyme and its expression is highly regulated. Both isozymes form prostaglandins that support physiologic functions; however, the formation of proinflammatory prostaglandins is catalyzed by Cox-2. Inhibition of Cox-2 accounts for the anti-inflammatory and analgesic action of non-steroidal anti-inflammatory drugs (NSAIDs).

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Differentiation: The process by which cells become more specialized to perform biological functions. Differentiation is a property that is often totally or partially lost by cells that have undergone malignant transformation.

Doppler Measurement (Inflammation): A method used to measure increased blood perfusion in an inflamed area in vivo, such as, but not limited to, in a model system, such as the histamine-skin model. Instruments such as the laser Doppler Velocimeter (LDV) and Acoustic Doppler Velocimeter (ADV) have been developed to measure velocity in a fluid flow. The LDV emits a light beam and the ADV emits an ultrasonic acoustic burse, and measure the Doppler shift in wavelengths from particles, such as red bold cells, moving with the flow. These methods measure flow at high precision and frequency and are non-invasive.

Effective amount or therapeutically effective amount: An amount, such as an amount of a fraction of blue-green alga (such as AFA or a species of Spirulina (Arthrospira), capable of decreasing inflammation, which can be determined by various methods used in the biological sciences. These methods include, but are not limited to, generating an empirical dose-response curve. In one embodiment, a "therapeutically effective amount" is an amount effective for reducing inflammatory cell migration. In another embodiment, a "therapeutically effective amount" is an amount effective for inhibiting NK cell activity. In still another embodiment, the "therapeutically effective amount" is an amount effective for inhibiting lipoxygenase activity.

A therapeutically effective amount also may be an amount sufficient for treating a condition or disease, such as an amount sufficient to relieve symptoms associated with inflammatory disorders, such as, but not limited to, asthma, arthritis, COPD, or allergy. For inflammation of the skin, redness, pain or swelling can be decreased. One of skill in the art can readily identify the symptoms associated with an inflammatory disorder or inflammation.

In one specific, non-limiting example, the effective amount of the fraction, such as an anti-inflammatory fraction of blue-green algae, is a dried form of the anti-inflammatory fraction, provided from about 0.01 to about 1.0 gram (gm) per kg body weight, such as about 0.05 to about 0.5 gm per kg body weight, or from about 0.1 to about 0.5 gm per kg body weight. In another specific, non-limiting, example the effective amount of the anti-inflammatory fraction of blue-green algae is from about 0.25 gm to about 5 gm, or from about 0.5 gm to about 5 gm, or from about 1 gm to about 2 gm. In one specific, non-limiting example, the effective amount of the anti-inflammatory fraction of blue-green algae is 1 gm. This effective amount may be administered at a given frequency, such as about once a week, about twice a week, about three times a week, once a day, about twice a day, about three times a day, or more.

The effective amount of a fraction of blue-green algae, such as an anti-inflammatory fraction of blue-green algae and frequency of administration may depend on a variety of factors, such as the genus or species of algae utilized, the general health of the subject being treated, and the physiological characteristics (e.g., height, weight, body fat percentage, metabolism, etc.) of the subject being treated.

Specific assays for determining an effective amount of a fraction of blue-green algae are provided herein. In one specific, non-limiting example, different amounts of an anti-inflammatory fraction of blue-green algae, such as AFA a species of Spirulina (Arthrospira), are consumed by human subjects and the presence and/or quantity of natural killer cells present in the circulatory system is detected and/or analyzed. In another embodiment, an animal (e.g. murine) model is utilized. The methods disclosed have equal application in medical and veterinary settings. Therefore, the general term "subject being treated" is includes all vertebrates (for example, but not limited to, humans, apes, dogs, cats, mice, rats, rabbits, sheep, pigs, and cows).

Endothelial Cell: A thin, flattened cell, a layer of them lines the inside surfaces of body cavities, blood vessels, and lymph vessels, making up the endothelium.

Extract. A concentrated preparation of a composition from an organism, such as a blue-green algae, or component thereof, obtained by removing active constituents of the composition with suitable solvents. In particular examples, an extract can be further concentrated by evaporating all or nearly all of the solvent, and adjusting the residual mass or powder to a pre-determined standard amount.

Fraction: A fraction of an organism, such as a species of blue-green algae, is any isolated or purified molecule or complex of molecules. A fraction can be obtained by any method known to the art by which molecules are isolated or purified from a cell, such as by extraction or ultacentrifugation. In particular examples, a fraction of blue-green algae, such as an anti-inflammatory fraction is produced by extraction of the blue-green algae cell followed by further isolation of molecules less than 100 kDa. In particular examples, a fraction is in liquid form. In other examples a fraction is in a solid form, such as a dried form. In still other examples, a fraction can be formulated as an inhalable particulate.

Glycoprotein: A complex molecule made of a protein moiety and a glycan or polysaccharide moiety.

Homing: The process of a cell migrating from the circulatory system into a tissue or organ. In some instances, homing is accomplished via tissue-specific adhesion molecules and adhesion processes.

$IC_{50}$: A measure of concentration used in chemistry and pharmacology. $IC_{50}$, or the half maximal inhibitory concentration, represents the concentration of an inhibitor that is required for 50% inhibition of its target (for instance, an enzyme (such as lipoxygenase), a cell, a receptor, or a microorganism). Generally, an $IC_{50}$ value is a measure of how much of a particular composition is needed to inhibit some biological process by 50%. $IC_{50}$ is commonly used as a measure of drug affinity, and represents the concentration of a composition that is required to obtain 50% of the maximum effect in vivo.

Immune Response: A response of a cell of the immune system, such as a B cell or T cell, to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFN-α, etc.), immunoglobulin production, dendritic cell maturation, and proliferation of a cell of the immune system. "Decreasing an immune response" or "anti-inflammatory activity" includes the use of any composition or method that results in an increase in any of these parameters. One of ordinary skill in the art can readily determine a decrease in any one of these parameters using known laboratory assays. In one specific non-limiting example, incorporation of $^3$H-thymidine can be measured to assess cell proliferation. A "substantial" decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease as compared to a control, such as a sample from a subject who has not been administered a test composition.

One of ordinary skill in the art can readily identify a significant decrease using known statistical methods. One, specific, non-limiting example of a statistical test used to assess a substantial decrease is the use of a Z test to compare the percent of samples that respond to compound or faction as compared to the percent of samples that respond using a control such as a carrier (for example, saline). A non-parametric ANOVA can be used to compare differences in the magnitude of the response induced by the compound or fraction alone as compared to the percent of samples that respond using the carrier. In this example, $p \leq 0.05$ is significant, and indicates a substantial decrease in the parameter of the immune response. One of skill in the art can readily identify other statistical assays of use.

Assays for immunosuppression and /or decreased inflammation will vary as a function of the disease application of interest. For some applications, such as potential treatment of arthritis, or decreased inflammation of the joints, the serum levels of circulating inflammatory cytokines will be measured using routine methods, such as ELISA or other immunoassay. These inflammatory cytokines include tumor necrosis factor alpha (TNFα) and type I interferons (IFNs), such as IFNα and IFNβ. For example, a significant decrease in circulating levels of one or more of these inflammatory cytokines as measured by ELISA or other immunoassays following treatment with a compound or faction of AFA indicates a successful immunosuppression treatment. For example, the circulating levels of one or more TNFα, IFNα and IFNβ can be measured prior to and following administration of the anti-inflammatory fraction of blue-green algae. The circulating levels can then be compared to determine if immunosuppression has occurred. In other examples, the level of these cytokines following treatment with a compound or faction can be compared to a reference value (such as a value that has been previously determined to be present in a subject in need of immunosuppression).

Immunologically Normal: "Immunologically normal" denotes a subject that displays immune system characteristics typical for the species to which the individual belongs. These typical characteristics include, among others, functioning B-cells and T-cells as well as structural cell components, called cell surface antigens, which act as the immunologic signature for a particular organism.

The use of such immunologically normal recipients means that an immunologically normal recipient's immune system, via its B-(humoral response) and T-(cellular response) cells, will identify the cell surface antigens of a foreign cell or an engrafted tissue as foreign. This recognition leads ultimately to an immune response against the cell or tissue, resulting in destruction of the cell or rejection of the graft. An immune response against an allogeneic tissue is known as host-versus-graft rejection.

Immunologically Compromised: An "immunologically compromised" subject has a genotypic or a phenotypic immunodeficiency. A genotypically-immunodeficient subject has a genetic defect that results in an inability to generate either humoral or cell-mediated responses. A specific, non-limiting example of a genotypically immunodeficient subject is a genotypically immunodeficient mouse, such as a SCID mouse or a bg/nu/xid mouse (Andriole et al., *J. Immunol.* 135:2911, 1985; McCune et al., *Science* 241:1632, 1988). A "phenotypically-immunodeficient subject" is a subject, which is genetically capable of generating an immune response, yet has been phenotypically altered such that no response is seen. In one specific, non-limiting example, a phenotypically-immunodeficient recipient is irradiated. In another specific, non-limiting example, a phenotypically-immunodeficient subject has been treated with chemotherapy. In yet another specific, non-limiting example, the phenotypically-immunodeficient subject has suffered a bacterial or viral infection, such as the human immunodeficiency virus (HIV) or simian immunodeficiency virus (SIV).

Immunomodulator: A molecule, such as a chemical compound, small molecule, steroid, nucleic acid molecule, or other biological agent, that can modulate an immune response. In some examples, an immunomodulator increases an immune response and has immunoenhancing activity. In additional examples, an immunomodulator decreases or suppresses an immune response and has immunosuppressant activity. Specific, non-limiting examples of immunomodulator are molecules that either decrease or increase an immune response by at least about a 10%, at least about a 20%, at least about 30%, at least about 40%, at least about 50%, at least about 60%, at least about 70% decrease, at least about 80%, or at least about 90%, for example relative to a control in the absence of the immunomodulator.

Immunosuppressive agent: A molecule, such as a chemical compound, small molecule, steroid, nucleic acid molecule, or other biological agent, that can decrease an immune response such as an inflammatory reaction. In some embodiments, the agent affects the migration and inflammatory activity of immune cells. In one embodiment, the agent is fraction extracted from blue-green algae.

Specific, non-limiting examples of additional immunosuppressive agents are non-steroidal anti-inflammatory agents, cyclosporine A, FK506, and anti-CD4. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide), a nonsteroidal anti-inflammatory drug (NSAIDs), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20). Rapamycin is an additional example of an immunosuppressive agent.

An immunosuppressive agent can be a compound, antibody, nucleic acid molecule, protein, glycoprotein, or cell, including neuropeptides and other signaling molecule that affects the migratory behavior of cells in tissue or recruitment of cells from the blood into tissue. One group of agents is described by chemotaxis, and includes compounds that attract inflammatory cells into an inflamed joint. Another group of agents includes anti-inflammatory compounds that reduce such migratory behavior, such as selective COX-2 inhibitors (CELEBREX®). In one specific example, the immunosuppressive agent that affects the migration of inflammatory cells is a fraction from blue-green algae.

Inflammation: When damage to tissue occurs, the body's response to the damage is usually inflammation. The damage may be due to trauma, lack of blood supply, hemorrhage, autoimmune attack, transplanted exogenous tissue or infection. This generalized response by the body includes the release of many components of the immune system (for instance, IL-1 and TNF), attraction of cells to the site of the damage, swelling of tissue due to the release of fluid and other processes. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process. An example of chonic inflammation is inflammatory arthritis.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Leukocytes: Cells in the blood, also termed "white cells," that are involved in defending the body against infective organisms and foreign substances. Leukocytes are produced in the bone marrow. Leukocytes can be divided into the polymorphonuclear leukocytes (neutrophils, eosinophils, basophils) and mononuclear leukocytes (monocytes and lymphocytes). There are two main types of lymphocytes: B-cell and T-cells. Natural killer cells are also sometimes called Large Granular Lymphocytes.

Lipoxygenase: An enzyme that catalyzes the oxygen-dependent oxidation of fatty acid substrates (linoleic acid and arachidonic acid are common examples) to form hydroperoxy-fatty acid products. Enzymes have been purified from diverse organisms that display a broad range of substrate specificity and product specificity (i.e. the site of oxidation within the fatty acid).

Lymphoproliferation: An increase in the production of lymphocytes.

Macrophages: A population of ubiquitously distributed mononuclear phagocytes responsible for numerous homeostatic, immunological, and inflammatory processes. Their wide tissue distribution makes these cells well suited to provide an immediate defense against foreign elements prior to leukocyte immigration. Inflammatory macrophages are present in various exudates, and can be characterized by various specific markers, such peroxidase activity and cytokine expression, and are derived from monocytes they share similar properties. "Activated macrophages" refers to macrophages possessing specifically increased functional activity. The process of differentiation is distinct from macrophage "activation," which is the process trough which differentiated macrophages acquire an increase ability to perform specific functions. Generally, unactivated macrophages are relatively quiescent immunologically, having low oxygen consumption, low levels of major histocompatibility complex (MHC) class II gene expression, and little or no cytokine secretion. Once activated, a macrophage has an inability to proliferate and has a high oxygen consumption. In addition, activated macrophages secrete cytokines such as TNF-α, IL-1 and IL-6.

Mammal: This term includes both human and non-human mammals. Similarly, the term "subject" includes both human and veterinary subjects.

Molecular Weight Distribution: This term indicates that the molecules existing within a composition are of varying molecular weights. In particular examples, the molecular weight distribution can be defined by a specific percentage, such that in a given molecular weight distribution, 90%, 95%, 98%, 99.5% or even 100% of the molecules in a fraction are below a specified molecular weight.

Monocyte: A large white blood cell in the blood that ingests microbes or other cells and foreign particles. When a monocyte passes out of the bloodstream and enters tissues, it develops into a macrophage.

Natural Killer Cells: Large granular lymphocytes that do not express T-cell antigen receptors (TCR) or Pan T marker CD3 or surface immunoglobulins (Ig) B cell receptor but that usually express the surface markers CD16 (FcγRIII) and CD56 in humans, and NK1.1/NK1.2 in certain strains of mice. NK cells can also express CD8.

Parenteral: Administered outside of the intestine, for instance, not via the alimentary tract. Generally, parenteral formulations are those that will be administered through any possible mode except ingestion. This term especially refers to injections, whether administered intravenously, intrathecally, intramuscularly, intraperitoneally, intra-articularly, or subcutaneously, and various surface applications including intranasal, intradermal, and topical application, for instance.

Pharmaceutical Agent or Drug: A chemical compound or composition capable of inducing a desired therapeutic or prophylactic effect when properly administered to a subject. Pharmaceutical agents include, but are not limited to anti-infective agents, such as antibiotics, anti-fungal compounds, anti-viral compounds, and hyper-immune globulin, anti-cancer agents, for instance, chemotherapeutics, immunosuppressive agents, for instance, non-steroidal anti-inflammatory agents, biological response modifiers, and disease-modifying antirheumatic drugs.

Pharmaceutically Acceptable Carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the blue-green algae and extracts described herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically Acceptable Salt: Salts formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002).

Polymorphonuclear (PMN) Cells: Immune white blood cells having a lobed nucleus. Neutrophils are one type of PMN cell.

Preventing or Treating a Disease: "Preventing" a disease refers to inhibiting the full development of a disease, for example in a person who is known to have a predisposition to a disease such as an autoimmune disorder. An example of a person with a known predisposition is someone with a history of rheumatoid arthritis in the family, or who has been exposed to factors that predispose the subject to a condition, such as lupus or arthritis. "Treatment" refers to a therapeutic intervention that ameliorates a sign or symptom of a disease or pathological condition after it has begun to develop.

Reactive Oxygen Species: Reactive oxygen species (ROS) are cytotoxic and mutagenic. ROIs modify and damage critical biomolecules including DNA and lipids. They are partial reduction products of oxygen: 1 electron reduces $O_2$ to form superoxide ($O_2^-$), and 2 electrons reduce $O_2$ to form hydrogen peroxide ($H_2O_2$). The cytotoxic property of ROS is exploited by phagocytes, which generate large amounts of superoxide and hydrogen peroxide as part of their armory of bactericidal mechanisms. ROS have been considered an accidental byproduct of metabolism, particularly mitochondrial respiration. Recent studies give evidence for regulated enzymatic generation of $O_2^-$, and its conversion to $H_2O_2$ in a variety of cells.

Several biological systems generate reactive oxygen. For example, exposure of neutrophils to bacteria or to various soluble mediators such as formyl-Met-Leu-Phe or phorbol esters activates a massive consumption of oxygen, termed the respiratory burst, to initially generate superoxide, with secondary generation of $H_2O_2$, HOCl and hydroxyl radical. The enzyme responsible for this oxygen consumption is the respiratory burst oxidase (nicotinamide adenine dinucleotide phosphate-reduced form (NADPH) oxidase).

Recruitment of a Cell: A process whereby a cell in the circulatory system migrates into a tissue or organ. Recruitment may be facilitated by a compound or molecule, such as a chemoattractant signal or cell receptor. For example, both CXCR4 and IL-8 have identified roles in PMN cell homing.

Subject: Living multi-cellular vertebrate organisms, a category that includes both human and non-human mammals. The methods and compositions disclosed herein have equal applications in medical and veterinary settings. Therefore, the general term "subject" is understood to include all animals, including, but not limited to, humans or veterinary subjects, such as other primates, dogs, cats, horses, and cows.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Anti-Inflammatory Fraction Isolated from Blue-green Algae Cells

Blue-green algae, such as *Aphanizomenon flos aquae* (AFA) or *Spirulina* (*Arthrospira*) can be fractionated. Processes for growing, harvesting, and concentrating blue-green algae cells are known to the art. Blue-green algae, such as AFA or *Spirulina* (*Arthrospira*), can be isolated from any source. The source can be a natural source of blue-green algae, such as a lake (for example Klamath Lake). The source can also be a man-made source of blue-green algae such as an artificial lake or water source. The source can also be bioreactors or fermentors. The source can be an environment produced to grow and harvest blue-green algae commercially.

The blue-green algae can be used directly, or can be stored as liquid, frozen liquid, dehydrated, freeze-dried, or dried using the method described below. In one embodiment, the blue-green algae are harvested and dried using DLT HYDRO.DRI™ Technology. The term "DLT HYDRO.DRI™ Technology," also known as REFRACTANCE WINDOW™ (RW) technology, refers to a system wherein the dryer utilizes the very properties of water to drive water out of the product. In brief, when water is placed over a heating source, heat gets dispersed in the water through convection. As it absorbs heat, water transmits infrared energy to the outside in three ways: evaporation, conduction, and radiation. If the surface of the water surface is covered by a transparent medium such as plastic, evaporation and its associated heat loss are blocked and only conduction occurs. The plastic membrane acts like a mirror reflecting infrared energy. When a moist material, such as wet blue-green algae is placed on the plastic surface, the water in the material creates a "window" that allows for the passage of infrared energy. It is believed that in this system the water in the material allows for radiation, conduction and evaporation all to occur, providing for exceptionally effective heat transfer. However after a few minutes, as the material dries, the infrared "window" closes and conduction remains the only means of heat transfer. Since plastic is a poor heat conductor, little heat is lost and transferred to the product. Therefore, when dried with DLT HYDRO.DRI™ Technology, algae are exposed to heat for only briefly.

In this drying system, liquid algae (cells suspended in solution) is placed on the surface of the dryer's conveyor belt. The belt is a food grade mylar (transparent polyester film) set on the surface of hot water. Heat from the circulating water is conducted to the belt and then into the water present in the product to be dried, gently speeding the natural process of evaporation while protecting natural nutrients. As the product dries and water evaporates, heat ceases to be transmitted to the product. Without being bound by theory, this prevents the degradation of polypeptides, nucleic acids, nutrients and pigments. Thus, the drying process maintains algae temperature far below the temperature of the circulating water beneath the conveyor belt.

Other drying systems can be used to produce dried algae. Generally, three factors play a role in the degradation of algae: degree of heat, exposure to oxygen, and exposure time to heat. Applying a high amount of heat for a short period of time results in less degradation of the components of the blue-green algae. In one example, heat, such as a temperature of about 65° C. to about 80° C., is applied, such as a temperature of about 70° C. to about 75° C., or about 72° C. The heat can be applied for a sufficient amount of time to dry the algae, such as about 1 to about 15 minutes, or for about 2 to about 10 minutes, or for about 3 to about 7 minutes. In one example, heat is applied to the algae at 72° C. for only 3 to 5 minutes. This process is known to one of skill in the art, and is fully described at the Desert LakeTechnology LLC website, and is described in Abonyi et al., "Evaluation of Energy Efficiency and Quality Retention for the REFRACTANCE WINDOW™ Drying System: Research Report, Washington State University, Pullman, Wash., Dec. 30,1999). However, freeze dried, vacuum dried, drum dried cells and spray-dried cells can also be utilized.

As disclosed herein, an extract can be prepared from fresh, dehydrated, or preserved blue-green algae cells. The algae can be extracted in any aqueous solution, such as with water or a suitable buffered salt solution. For example, buffered solutions, generally of a neutral pH (about pH 7.0 to about pH 7.8, such as about pH 7.2 to about pH 7.6, or about pH 7.4) are utilized. Suitable buffered salt solutions are well known in the art and include phosphate buffered saline and commercially available culture media. The aqueous extraction is generally performed below room temperature (generally 25° C.), such as at temperatures of about 3° C. to about 15° C., such as at about 4° C. to about 10° C., or at about 4° C., but the extraction can also be performed at room temperature (about 25° C.). As used in this context, "about" refers to within 1-2° C.

The algae can also be extracted using other solvents. The solvents include alcohols, such as ethanol and methanol, and DMSO. The extract may be produced by any other suitable method. For example, extraction can be performed with water, dilute acids, certain organic solvents, including mixtures thereof with water, or supercritical fluids (e.g., supercritical carbon dioxide). In some embodiments, the extraction process does not include the use of ethanol or methanol. In some embodiments, extraction is followed by drying, as described above. Illustrative extract solvents include alkanols such as methanol or ethanol, mixtures of methanol or ethanol with water, chloroform or hexane. Solvents also include water or buffered saline solutions of a pH of about 7.0 to 7.8. The extraction can occur at any temperature such as, for example, about 10° C. to about 150° C., more particularly about 4° C. to about 50° C., such as about 4° C. to about 30° C., such as about 4° C. to about 25° C., or at about 20° C. to about 25° C. The extract can be heated to concentrate the extract, such as using a temperature of about 65° C. to about 80° C., such as a temperature of about 70° C. to about 75° C., or about 72° C. This can be continued for the appropriate time to obtain the desired amount of extract concentrate.

In one example, one gram of dried algal material is suspended in 10 mL of a buffered salt solution, such as phosphate-buffered saline, and incubated for 20 minutes at 20° C. under constant gentle agitation. The algae suspended in the buffered salt solution can be protected from light to decrease degradation of light-sensitive compounds. Following incubation in an aqueous solution, the solid material is separated from the aqueous extract, such as by filtration or centrifugation. In particular examples, the mixture of algae in the buffered salt solution can be mixed by repeated inversion of the vial, and centrifuged to remove solid material. For example, the suspension can be centrifuged at 400 g for 10 minutes.

Following separation of the solid material, the supernatant, which generally appears blue in color, is isolated. This supernatant is then used for removal of high-molecular weight compounds, such as phycocyanin, and enrichment of low molecular weight compounds. This can for example be performed by centrifugation over an ultra filtration filter with a specified molecular weight cut-off, which is designed to only allow low molecular weight compounds to penetrate through the filter, and which retains larger compounds above the filter. In one example, a bright yellow filtrate is decanted following centrifugation, and sterile filtered using a 0.22 mm filter. This filtrate can be stored, such as at about 4° C. in the dark.

As disclosed herein, the filtration can be performed using ultra filtration filters having different molecular weight cut-offs, such as a filter with a 100 kDa cut-off that allows collection of molecules of less than about 100 kDa, and excludes molecules of about 100 kDa or greater; a filter with a 50 kDa cut-off that allows collection of molecules less than about 50 kDa, and excludes molecules of about 50 kDa or greater; a filter with a 30 kDa cut-off that allows collection of molecules less than about 30 kDa, and excludes molecules of about 30 kDa or greater; a filter with a 10 kDa cut-off that allows collection of molecules less than about 10 kDa, and excludes molecules of about 10 kDa or greater; a filter with a 5 kDa cut-off that allows collection of molecules less than about 5 kDa, and excludes molecules of about 5 kDa or greater; or a filter with a 3 kDa cut-off that allows collection of molecules less than about 3 kDa, and excludes molecules of about 3 kDa or greater. In this context, "about" refers to a difference of 0.5 daltons. In other examples, the molecular weight cut-off filter allows collection of molecules that are less than 100 kDa, and excludes molecules of 100 kDa or greater; less than 50 kDa, and excludes molecules of 50 kDa or greater; less than 30 kDa, and excludes molecules of 30 kDa or greater; less than 10 kDa, and excludes molecules of 10 kDa or greater; less than 5 kDa, and excludes molecules of 5 kDa or greater; or less than 3 kDa, and excludes molecules of 3 kDa or greater.

In addition to molecular weight cut-off filtration, other means of isolating a blue-green algae fraction containing low molecular weight compounds can be utilized, such as High Performance Liquid Chromatography or Fourier-Transform mass spectroscopy. Thus, in several embodiments, the anti-inflammatory fraction can be isolated, for example, by chromatographic or spectroscopic methods such that it contains components less than about 100 kDa, and does not contain components that are about 100 kDa or greater; less than about 50 kDa, and does not contain components that are about 50 kDa or greater; less than about 30 kDa, and does not contain components that are about 30 kDa or greater; less than about 10 kDa, and does not contain components that are about 10 kDa or greater; less than about 5 kDa, and does not contain components that are about 5 kDa or greater; or less than about 3 kDa, and does not contain components that are about 3 kDa or greater. Thus, depending on the embodiment components (such as proteins and glycoproteins) about 100 kDa or greater, about 50 kDa or greater, about 30 kDa or greater, about 10 kDa or greater, about 5 kDa or greater, or about 3 kDa or greater, respectively, are not present in the anti-inflammatory fraction.

One of skill in the art will appreciate that the fractionation techniques used to produce the low molecular weight molecules described herein may allow a small percentage of larger-sized molecules into the fraction. In particular examples, the fraction comprises a molecular weight distribution wherein at least 90%, 95%, 98%, or 99.5% of the molecules in the isolated fraction are less than a cut-off weight and the cut-off weight is about 100 kDa. In other examples, the cut-off weight is 50 kDa, 30 kDa, 10 kDa, 5 kDa, or 3 kDa.

Phycocyanin is a multisubunit pigmented protein complex generally present in blue-green algae in a high molecular weight complex greater than 100 KDa. Phycocyanin absorbs light at 620 nm and emits fluorescence at about 650 nm. Accordingly, the presence of phycocyanin in a composition can be determined by its light absorbing and emitting properties.

The anti-inflammatory fraction purified from AFA and *Spirulina (Arthrospira)* described herein is substantially free of phycocyanin. Likewise, compositions described herein comprising the anti-inflammatory fraction from AFA *Spirulina (Arthrospira)* are substantially free of phycocyanin. As used herein, "substantially free of phycocyanin" means that the fraction and the composition can contain a concentration of phycocyanin that is less than about 0.1 mg/L, less than about 1 mg/L, or less than about 5 mg/L. The presence of phycocyanin can be measured by any means known to one of skill in the art. For example, the concentration of phycocyanin can be measured by spectrophotometry, and reading light absorption at 620 nm.

In yet a further example, the anti-inflammatory fraction inhibits lipoxygenase. Several assay procedures have been published in the literature for measuring lipoxygenase activity. The simplest assay is the spectrophotometric monitoring of lipoxygenase-mediated production of a hydroperoxy-fatty acid. The hydroperoxy-moiety absorbs light at 234 nm and can therefore be easily monitored with a spectrophotometer. Another method of assaying for lipoxygenase activity is to monitor the consumption of oxygen using a Clark electrode. Another assay that has been used is to determine the concentration of hydroperoxy (or the chemically-reduced hydroxy-derivatives) fatty acids by separation from the substrate on a high-performance liquid chromatography (HPLC) system (for example, Yamamoto et al., *Methods in Enzymology*, 186, 371-380, 1990). Two different colorimetric assay formats have been developed that utilize the oxidation state of the hydroperoxy product to couple product formation to color formation. Both assays are conducted in two steps and differ in the colorimetric reagent. After product has been formed, the color-forming reagent is added and the color is measured on a spectrophotometer. One assay uses a xylenol orange:iron (II) complex (Waslidge et al., *Anal. Biochemistry*, 231:354-358, 1995) and the second assay uses hemoglobin (as the catalyst) and N-benzoyl leucomethylene (Auerbach et al., *Anal. Biochemistry*, 201:375-380, 1992) as the colorimetric reagent. These assays offer improved sensitivity over the direct spectrophotometric assay (~10-fold) and improved throughput when compared to the HPLC method. Kratky et al. have published a very sensitive assay of lipoxygenases based upon chemiluminescent detection (Kratky et al., *Biochimica et Biophyscia Acta*, 1437:13-22, 1999). The hydroperoxy-fatty acid product of lipoxygenase is reacted with isoluminol and microperoxidase to form an electronically excited form of 4-aminophthalate that emits a photon upon its decay. Molecular Probes (now part of Invitrogen) has published an assay for hydrogen peroxide detection that employs AMPLEX RED® (N-acetyl-3,7-dihydroxyphenoxazine) or AMPLEX ULTRARED® and uses horseradish peroxidase as the redox catalyst instead of microperoxidase (*Zhou et al., Anal. Biochemistry*, 253:162-168, 1997). One of skill in the art can readily use any of these assays to detect lipoxygenase activity.

The anti-inflammatory fraction inhibits lipoxygenase activity as compared to a control. For example, the anti-inflammatory fraction can decrease lipoxygenase activity by at least about a 10%, at least about a 20%, at least about 30%, at least about 40%, at least about 50%, at least about 60%, at least about 70%, at least about 80%, or at least about 90% decrease, relative to a control. The control can be lipoxygenase activity in the absence of any additional components, lipoxygenase activity in the presence of carrier alone, or a standard value. In another embodiment, the control is a high molecular weight fraction of a blue-green algae, such as an aqueous fraction including components with a molecular weight of greater than about 100 kDa, greater than about 50 kDa, greater than about 10 kDa or greater than about 5 kDa, and which includes greater than 5 mg/L phycocyanin. Statistical analyses that are well known in the art, for example a Student's T-test, can be used to determine if an inhibition in enzymatic activity is significant.

In another example, the anti-inflammatory fraction activates natural killer (NK) cells and inhibits migration and inflammatory activities of polymorphonuclear (PMN) cells. Biological methods of well known for measuring NK cell activation and other inflammatory activities of PMN cells. For example, blood cells, such as purified NK cells can be treated with a fraction of interest, and then monoclonal antibodies (such as monoclonal antibodies that specifically bind CD3, CD56, CD69 and/or CD25 are used. These antibodies can be fluorescently labeled, or labeled secondary antibodies can be utilized. In one non-limiting example, to measure NK cell activation, PBMC are treated with serial dilutions of an anti-inflammatory fraction, such as 1117 (see the examples)

for about 16 to about, 24 hours, and then immunostained with fluorescence-conjugated monoclonal antibodies that specifically bind CD3, CD56, and CD69 or CD25. Multi-parameter flow cytometry is used to measure particle size and granularity, and the expression levels of each of the three cell surface markers is evaluated by measuring fluorescence intensity for each fluorescent marker. The NK cells are analyzed by electronic gating on the CD3-negative, CD56-positive population. The expression level of CD69 or CD25 is measured as a function of the fluorescence intensity. The increase in fluorescence, as a measure of expression of activation markers, can be increased by at least about a 10%, at least about a 20%, at least about 30%, at least about 40%, at least about 50%, at least about 60%, at least about 70%, at least about 80%, or at least about 90%, for example, relative to a control. The control can be NK activity in the absence of any additional components, NK activity in the presence of carrier alone, or a standard value.

In yet another example, the anti-inflammatory fraction decreases action of inflammatory cytokines, such as interleukin (IL)-1 and tumor necrosis factor (TNF-α). One of skill in the art can readily measure the amount of cytokines, using a variety of assays. Suitable assays include immunoassays. For example, cytokine expression or activity can be decreased by at least about a 10%, at least about a 20%, at least about 30%, at least about 40%, at least about 50%, at least about 60%, at least about 70%, at least about 80%, or at least about 90%, for example relative to a control. The control can be cytokine expression in the absence of any additional components, cytokine expression or activity in the presence of carrier alone, cytokine expression in response to a known stimulus such as a mitogen or inflammatory mediator, or a standard value. Cytokines include IL-1, IL-2, IL-4, IL-6, IL-10, IL-12, members of the interferon family, tumor necrosis factor (TNF), and others. Methods are well known to evaluate cytokine expression, such as ELISPOT assays, biological assays, and PCR methods.

The extracts disclosed herein can be fractionated by any suitable method such as molecular weight filtration; chromatography, liquid-liquid extraction or solid-phase extraction. Illustrative chromatography methods include column chromatography with silica gel, florosil, silicic acid, octadecyl silica, polyamide, ion exchange materials, and mixtures thereof. The chromatography may be performed with a series of successive eluants including water, dilute acids or alkalis, certain organic solvents, or supercritical fluids. Illustrative eluants include alkanes (e.g., hexane), chloroform, esters (e.g., ethylacetate), alkanols (e.g., methanol, ethanol, butanol), acetone, acetonitrile, tetrahydrofuran or aqueous buffer solutions. The fractionation can occur at any temperature such as, for example, about 4° C. to about 100° C., more particularly about 18° C. to about 30° C., and may be continued for the appropriate time to obtain the desired amount of extract fraction concentrate.

The fractions can be subjected to further processing for identifying and purifying additional therapeutically-active compounds. For example, AFA or *Spirulina* (*Arthrospira*) can be extracted with water, a buffered salt solution, ethanol (or any other solvent) as described above and in the examples below, and a size-exclusion chromatography can be performed. The resulting fraction has components of a molecular weight of less than about 100 kDa, and not 100 kDa or greater; less than about 50 kDa, and not 50 kDa or greater; less than about 30 kDa, and not 30 kDa or greater; less than about 10 kDa, and not 10 kDa or greater; less than about 5 kDa, and not 5 kDa or greater; or less than about 3 kDa, and not 3 kDa or greater. The resulting fraction can be dried using rotary evaporation and a centrifugal evaporator, and resuspended in a solvent, such as, but not limited to, deionized water. Extracts, or fractions thereof, can be profiled by TLC (thin layer chromatography) and HPLC (high performance liquid chromatography). Column chromatography may be used to fractionate the mixture of chemicals found in AFA or *Spirulina* (*Arthrospira*) extracts. Fractionation of extracts can involve normal phase, reversed phase or polyamide stationary phases using vacuum liquid chromatography (VLC) for crude fractionation, flash column chromatography for finer separations and preparative TLC or preparative HPLC for compound isolation and purification using standard methods (Houghton et al., Laboratory Handbook for the Fractionation of Natural Extracts (1998)) and specific HPLC separations for components of AFA (see Schaneberg et al., *Pharmazie* 58:381-384, 2003). The identity of compounds isolated may be determined initially by comparison of chromatographic (TLC, HPLC) and spectroscopic (ultra-violet visible (UV-VIS) spectroscopy and mass spectrometry (MS)) data to known reference compounds. Stand-alone or HPLC-linked spectrometers could be used. Electrospray (see Mauri et al., *J. Pharm. Biomed. Anal.*, 23:61-68, 2000) and other spectroscopic data of known compounds can be obtained from the literature. For novel compounds, UV-VIS spectra and MS can determine the presence of chromophores and molecular weight, respectively. Infra-red (IR) spectroscopy can provide functional group information and most importantly, 1-D and 2-D proton and carbon-13 nuclear magnetic resonance (NMR) spectroscopy can be used for total structure determination. Polarimetry may be used for chiral molecules to determine stereochemistry (if reference data is available) or simply to characterize the compound. Quantitative HPLC analytical protocols can be developed to assess the concentration of known components. The method of normalization (peak area of each component expressed as % of total areas) can be used for unknowns. Changes in the relative concentration of components would be monitored regularly (at least every 3 months); materials showing greater than 10% change will be deemed to have decomposed.

As discussed below, any active compound of dried fraction can be resuspended in a pharmaceutically acceptable carrier, and used in the methods disclosed herein.

Methods for Reducing Inflammation

Methods are described herein for decreasing inflammation in a subject. The subject can have inflammation of any organ, including organs of the digestive system, skin, nervous system, lymph system, cardiovascular system, or endocrine system. In some examples, inflammation of the joints or skin can be treated using the presently described methods. The inflammation can be acute or chronic. The subject can be any subject of interest, including healthy or immunocompromised subjects. Methods are also described herein for reducing an inflammatory response in vitro, such as in cultures of isolated animal cells. The subject can be a human or a veterinary subject.

In some embodiments, the subject is suffering from a disease or physiological condition, such as inflamed joints or muscles. In certain embodiments, the subject suffers from inflammation of mucosal surfaces, such as canker sores, or hemorrhoids. In certain embodiments, the subject suffers from a disease or condition of the skin, such as acne, psoriasis, herpes sores, or allergic reactions, including reactions to poison ivy, and insect bites. In some embodiments, the subject has an allergy, asthma, arthritis or colitis. In some embodiments, the subject is suffering from an acute inflammatory condition, such an acute allergic reaction or sprains, bruises and muscle damage from sports-injury or accidents, or sunburn. In one example, the subject is suffering from inflammation related to the natural progression of the menstrual cycle, but leading to excessive pain and cramps. In specific embodiments, the subject suffers from any inflammatory diseases and conditions. In some embodiments, the subject has an allergy, asthma, atherosclerosis, dermatitis (such as allergic chronic contact dermatitis and environmental chronic contact dermatitis), laminitis, reactive airway diseases and processes (such chronic obstructive pulmonary disease ("COPD"), inflammatory airway disease ("IAD"), inflammatory bowel disease, and rheumatoid arthritis, ulcerative colitis, Crohn's disease, stroke-induced brain cell death, traumatic brain injury, ankylosing spondylitis, fibromyalgia. Autoimmune diseases that include inflammation, such as multiple sclerosis, systemic lupus erythematosus, scleroderma, systemic sclerosis, and Sjögren's syndrome can also be treated using the methods disclosed herein.

Generally the methods disclosed herein include the use of an effective amount of a composition comprising an anti-inflammatory fraction of blue-green algae (AFA and/or Spirulina (Arthrospira) species) as described herein, or dried form thereof. The anti-inflammatory fraction from blue-green algae, or dried form thereof can be provided alone or can be provided as a part of a composition including a pharmaceutically acceptable carrier. Thus, a method is provided herein for reducing an inflammatory reaction in a subject, comprising administering a therapeutically effective amount of the anti-inflammatory fraction, or dried form thereof, alone or with other therapeutic agents, thereby decreasing inflammation, which can be measured as described above.

A method of treating an allergic reaction is provided herein. The reaction can be systemic or localized. An allergy is a collection of symptoms caused by an exaggerated immune response or reaction to substances that do not trigger an immune response in most people. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions which could be provoked by many antigens. In practice these types do not necessarily occur in isolation from each other.

Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms.

Methods are provided for treating allergic reactions that include administering to a subject having or at risk of developing an allergic reaction a therapeutically effective amount of a composition comprising an anti-inflammatory fraction of blue-green algae, or dried form thereof. The administration can be systemic or local. For example, for treating an allergic reaction of the skin, the anti-inflammatory fraction of blue-green algae, or dried form thereof, can be administered topically.

Methods are also disclosed herein for treating or preventing inflammatory lung disease in a subject. Inflammatory lung diseases include, but are not limited to pneumonia, ARDS, respiratory distress of prematurity, chronic bronchitis, chronic obstructive pulmonary disease (COPD), cystic fibrosis, pulmonary fibrosis, and pulmonary sarcoidosis. The method includes administering a therapeutically effective amount of the anti-inflammatory fraction, or dried form thereof, to a subject having or at risk of developing inflammatory lung disease, thereby treating or preventing the inflammatory lung disease. In one embodiment, the anti-inflammatory fraction, or dried form thereof, can be administered locally, such as by inhalation. In another embodiment, the anti-inflammatory fraction, or dried form thereof, is administered systemically, such as by intravenous injection.

Local administration of the anti-inflammatory fraction, or dried form thereof, is performed by methods well known to those skilled in the art. By way of example, one method of administration to the lungs of an individual is by inhalation through the use of a nebulizer or inhaler. For example, the anti-inflammatory fraction, or dried form thereof, is formulated in an aerosol or particulate and drawn into the lungs using a standard nebulizer well known to those skilled in the art.

The effectiveness of treatment with the anti-inflammatory fraction, or dried form thereof, can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. An increase in one or more of these parameters indicates efficacy of treatment.

The methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second (FEV1), allows bronchoconstriction to be quantitatively evaluated. An increase in FVC or FEV1 reflects a decrease in bronchoconstriction, and indicates that the anti-inflammatory fraction is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, an increase in the FEF 25-75 or FEV1 reflects a decrease in bronchoconstriction, and indicates that the anti-inflammatory fraction is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, an increase in the peak expiratory flow following administration of the anti-inflammatory fraction, or dried form thereof, indicates that the therapy is effective.

Methods are also disclosed herein for the treatment of arthritis. Arthritis is an inflammatory disease that affects the synovial membranes of one or more joints in the body, is the most common type of joint disease. Billions of dollars are spent annually for the treatment of arthritis and for lost days of work associated with the disease. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

One type of arthritis is reactive arthritis, which is an acute nonpurulent arthritis secondary to a urinary tract or gastrointestinal infection with a variety of microorganisms, including *Chlamydia trachomatis, Yersinia, Salmonella, Shigella*, and *Campylobacter*. Microbial components (and not live organisms) are found in the affected joints. The arthritis appears abruptly and tends to involve the knees and ankles, but sometimes involves the wrists, fingers, and/or toes. Untreated, the arthritis lasts for about a year, then generally abates and only rarely is accompanied by ankylosing spondylitis. Despite evidence of disease being triggered by bacterial infection, viable bacteria are rarely present in affected joints and antibiotic treatment seldom provides relief.

Up to 16% of subjects with gastrointestinal (GI) infection by *Salmonella* or *Shigella* subsequently develop arthritis. Despite this temporal association, it is unclear whether live bacteria reaching the affected joint are the cause of this arthritis. To date, success in culturing viable microorganisms from the affect joints has been quite limited, and antibiotic treatment rarely is of benefit. Symptomatic treatment is often accomplished with high doses of non-steroidal anti-inflammatory agents. In addition, intra-articluar steroid injections are of use. However, a need remains for additional therapies for this disease.

Rheumatoid Arthritis (RA) is a chronic, systemic, inflammatory disease that affects the synovial membranes of multiple joints. RA considered an acquired autoimmune disease, and genetic factors appear to play a role in its development. In most cases of RA, the subject has remissions and exacerbations of the symptoms. Rarely does the disease resolve completely, although at times the symptoms might temporarily remit.

A method is disclosed herein for treating or preventing an inflammatory arthropathy in a subject. The method includes administering a therapeutically effective amount of the anti-inflammatory fraction, or dried form thereof, to a subject having or at risk of developing an inflammatory arthropathy, such as arthritis, thereby treating or preventing the inflammatory arthropathy. In one embodiment, the anti-inflammatory fraction, or dried form thereof, can be administered locally, such as by intra-articular injection. In another embodiment, the anti-inflammatory fractions, or dried form thereof, can be administered systemically.

Local administration of the anti-inflammatory fraction, or dried form thereof, for the treatment of arthritis is performed by methods well known to those skilled in the art. By way of example, one method of administration to the knee, hip and/or shoulder of an individual is by intra-articular injection. For administration to the knee, for example, the joint to be injected is washed with a betadine solution or other antiseptic. A solution of an anesthetic, such as about one percent lidocaine hydrochloride is injected into the skin and subcutaneous tissue. A 3-way stopcock/needle assembly is utilized to administer the compound via an 18-30 gauge needle. The anti-inflammatory fraction, or dried form thereof, is injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient is then confined to bed for approximately 24 hours to minimize movement and minimize leakage of the anti-inflammatory fraction from the joint.

Methods are also disclosed for decreasing cytokine or chemokine production. In some embodiments, the methods include administering to the subject a therapeutically effective amount of the anti-inflammatory fraction, or dried form thereof, as described above, thereby reducing the production of cytokines or chemokines in the subject. In other embodiments, the methods include contacting cells in vitro. Cytokine levels in body fluids or cell samples can be measured following administration of the anti-inflammatory fraction by conventional methods known by those of skill in the art. For example, cytokine concentrations in cell culture supernatants and BAL fluid can be measured as recommended by the manufacturer of ELISA kits (R&D systems, Minneapolis, MN). Administration can be systemic or local.

Also disclosed are methods of reducing the infiltration of neutrophils in a subject. The methods include administering to the subject in need of treatment a therapeutically effective amount of an anti-inflammatory fraction of blue green algae, or dried form thereof. In particular examples, the methods can include assessing the effect of the anti-inflammatory fraction on neutrophil infiltration. Methods of measuring neutrophil infiltration are well known to those of skill in the art. For example, measurement of myeloperoxidase activity is often used as a marker of neutrophils infiltration into tissues. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration, and can serve as a measure of efficacy.

Regardless of how an anti-inflammatory fraction of blue green algae, or dried form thereof, is provided or administered, the methods disclosed herein can result in a transient relief from acute or chronic inflammation, such as a reduction in pain, redness, itching, or swelling. Reduction of inflammation can be determined by measuring the changes in a subject's temperature (systemic or local), redness, blood flow, swelling, or other ways to physically measure effects of inflammation. Also, reduction in inflammation can be measured by taking blood samples for evaluation of inflammatory markers in serum, plasma, or cells. For example, C-reactive protein, one or more cytokines, prostaglandins, or lipid peroxidation status can be measured, and a reduction in the above markers will indicate a reduction in inflammation. Reduction of inflammation may also be recorded by questionnaires pertaining to pain, itching, or other subjective measures related to inflammation.

In one embodiment, providing the anti-inflammatory fraction from blue-green algae, or dried form thereof, to a subject will reduce some signs or symptoms of inflammation in that subject within a certain time period, such as less than about 5 hours, less than about 4 hours, less than about 2 hours, less than about 1 hour, less than about 30 minutes, or less than about 10 minutes following administration.

Compositions comprising the described anti-inflammatory fraction, or dried form thereof, including compositions comprising one or more pharmaceutically acceptable carriers are thus provided for both local (such as topical or inhalational) and/or systemic (such as oral or intravenous) use to treat the various inflammatory conditions descried herein. Therefore, the disclosure includes within its scope pharmaceutical compositions comprising the anti-inflammatory fraction formulated for use in human or veterinary medicine. While the anti-inflammatory fraction, or dried form thereof, will typically be used to treat human subjects, it may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

In one embodiment, a therapeutically effective amount of the anti-inflammatory fraction, or dried form thereof, is formulated for administration to the skin. Formulations suitable for topical administration can include dusting powders, ointments, cremes, gels or sprays for the administration of the active compound to cells, such as skin cells. Such formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or combinations thereof.

In one example, the anti-inflammatory fraction, or dried form thereof, can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream which can be applied either to the face or to the scalp and hair, as well as to the human body, in particular those portions of the body that are chronically exposed to sun.

In some cosmetic formulations, additives can be included such as, for example, preservatives, bactericides, perfumes, antifoams, dyes, pigments which have a coloring action, surfactants, thickeners, suspending agents, fillers, moisturizers, humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can be chosen from the following group of substances: mineral oils, mineral waxes, such as triglycerides of capric or of caprylic acid, castor oil; fats, waxes and other natural and synthetic fatty substances, esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the present disclosure include alcohols, diols or polyols of low C number and ethers thereof, such as ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, such as silicon dioxide, aluminium silicates, polysaccharides and derivatives thereof, for example hyaluronic acid, xanthan gum and hydroxypropylmethylcellulose, or poly-acrylates.

An exemplary cosmetic formulation is as an additive to a sunscreen composition as a lotion, spray or gel, for administration to the skin to prevent or treat inflammation. A sunscreen can additionally include at least one further UVA filter and/or at least one further UVB filter and/or at least one inorganic pigment, such as an inorganic micropigment. The UVB filters can be oil-soluble or water-soluble. Oil-soluble UVB filter substances can include, for example: 3-benzylidenecamphor derivatives, such as 3-(4-methylbenzylidene)camphor and 3-benzylidenecamphor; 4-aminobenzoic acid derivatives, such as 2-ethylhexyl 4-(dimethylamino)benzoate and amyl 4-(dimethylamino) benzoate; esters of cinnamic acid, such as 2-ethylhexyl 4-methoxycinnamate and isopentyl 4-methoxycinnamate; derivatives of benzophenone, such as 2-hydroxy-4-methoxybenzophenone, 2-hydroxy-4-methoxy-4'-methylbenzophenone and 2,2'-dihydroxy-4-methoxybenzophenone; esters of benzalmalonic acid, such as di(2-ethylhexyl)4-methoxybenzalmalonate. Water-soluble UVB filter substances can include the following: salts of 2-phenylbenzimidazole-5-sulphonic acid, such as its sodium, potassium or its triethanolammonium salt, and the sulphonic acid itself; sulphonic acid derivatives of benzophenones, such as 2-hydroxy-4-methoxybenzophenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)benzenesulphonic acid and salts thereof. The list of further UVB filters mentioned which can be used in combination with the active agent(s) according to the disclosure is not intended to be limiting.

For treatment of the skin, a therapeutically effective amount of at the anti-inflammatory fraction, or dried form thereof, also can be locally administered to only an affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the anti-inflammatory fraction, or dried form thereof, can be administered in a composition that contains a synthetic or natural hydrophilic polymer as the carrier. Examples of such polymers include hydroxypropyl cellulose and polyethylene glycol. The anti-inflammatory fraction, or dried form thereof, can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of the anti-inflammatory fraction, or dried form thereof can also be incorporated into bandages.

In particular examples, the anti-inflammatory fraction, or dried form thereof, can be formulated for administration by inhalation, such as, but not limited to, formulations for the treatment of asthma. Inhalational preparations include aerosols, particulates, and the like. In general, the goal for particle size for inhalation is about 1 µm or less in order that the pharmaceutical reach the alveolar region of the lung for absorption. However, the particle size can be modified to adjust the region of disposition in the lung. Thus, larger particles can be utilized (such as about 1 to about 5 µm in diameter) to achieve deposition in the respiratory bronchioles and air spaces. In addition, oral formulations may be liquid (e.g., syrups, solutions, or suspensions), or solid (e.g., powders, pills, tablets, or capsules).

For administration by inhalation, the anti-inflammatory fraction, or dried form thereof, can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The compositions or pharmaceutical compositions also can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. When the anti-inflammatory fraction, or dried form thereof, is provided as parenteral compositions, e.g. for injection or infusion, the liquid anti-inflammatory fraction can be diluted, or the dried form of the anti-inflammatory fraction is generally suspended. This can be done in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

The anti-inflammatory fraction, or dried form thereof, is also suitably administered by sustained-release systems. Suitable examples of sustained-release formulations include suitable polymeric materials (such as, for example, semipermeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release formulations may be administered orally, rectally, parenterally, intracistemally, intravaginally, intraperitoneally, topically (as by powders, ointments, gels, drops or transdermal patch), bucally, or as an oral or nasal spray.

Preparations for administration can be suitably formulated to give controlled release of the anti-inflammatory fraction over an extended period of time. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the anti-inflammatory fraction can take the form of, for example, the dried form of the anti-inflammatory fraction included in tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutically acceptable carriers and excipients useful in these methods are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

Generally, the formulations are prepared by contacting the anti-inflammatory fraction, or the dried form thereof uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise the anti-inflammatory fraction, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. As disclosed herein, therapeutically effective amounts of the anti-inflammatory fraction, or dried form thereof, is of use for preventing development of an inflammatory reaction such as arthritis, asthma or an allergic reaction, or for treating these disorders. Administration may begin whenever the regression or prevention of disease is desired, for example, at a certain age of a subject, or prior to an environmental exposure.

The therapeutically effective amount of the anti-inflammatory fraction, or dried form thereof, will be dependent on the subject being treated, the severity and type of the affliction, and the manner of administration. For example, a therapeutically effective amount of a dried anti-inflammatory fraction of blue green algae can vary. For example, a dried form of the anti-inflammatory fraction can be provided from about 0.01 to about 1.0 gram (gm) per kg body weight, such as about 0.05 to about 0.5 gm per kg body weight, or from about 0.1 to about 0.5 gm per kg body weight. In another specific, non-limiting example the effective amount of the anti-inflammatory fraction of blue-green algae is from about 0.25 gm to about 5 gm, of from about 0.5 gm to about 5 gm, or from about 1 gm to about 2 gm. In one specific, non-limiting example, the effective amount of the anti-inflammatory fraction of blue-green algae is 1 gm. This effective amount may be administered at a given frequency, such as about once a week, about twice a week, about three times a week, once a day, about twice a day, about three times a day, or more. The exact dose is readily determined by one of skill in the art based on clinical factors such as the disorder being treated, and/or the age, weight, sex and physiological condition of the subject. A therapeutically effective amount of the anti-inflammatory fraction, or dried form thereof, can be administered with a therapeutically effective amount of another agent, such as a cytokine, a chemokine, or an immunosuppressive agent.

The anti-inflammatory fraction, or dried form thereof, can be administered in conjunction with a steriodal anti-inflammatory agent or a non-steroidal anti-inflammatory agent. Steroidal anti-inflammatory agents include gluccocorticiods, dexamethasone, prednisone, and hydrocortisone. Non steriodal antiflammator agents include Salicylates (such as Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate. Salicylamide) Arylalkanoic acids (such as Diclofenac, Aceclofenac, Acemethacin, Alclofenac Bromfenac, Etodolac, Indomethacin, Nabumetone, Oxametacin, Proglumetacin, Sulindac, Tolmetin), 2-Arylpropionic acids (such as Ibuprofen, Alminoprofen, Carprofen, Dexibuprofen, Dexketoprofen, Fenbufen, Fenoprofen, Flunoxaprofen, Flurbiprofen, Ibuproxam, Indoprofen, Ketorolac, Loxoprofen, NaproxenOxaprozin, Pirprofen, Suprofen, Tiaprofenic acid), N-Arylanthranilic acids (such as Mefenamic acid, Flufenamic acid, Meclofenamic acid, Tolfenamic acid) Pyrazolidine derivatives (such as Phenylbutazone, Ampyrone, Azapropazone, Clofezon,e Kebuzone, Metamizole, Mofebutazone, Oxyphenbutazone, Phenazone, Sulfinpyrazone) Oxicams (such as Piroxicam, Droxicam, Lornoxicam, Meloxicam, Tenoxicam or COX-2 inhibitors.

The disclosure is illustrated by the following non-limiting Examples.

EXAMPLES

Example 1

Production of the 1117 Fraction from AFA

A blue-green algae, *Aphanizomenon flos aquae* (AFA), was isolated from Klamath Lake. The blue-green algae were dried using DLT HYDRO.DRI™ Technology.

One gram of dried algal material was resuspended in 10 ml phosphate-buffered saline or water, and incubated 1 hour at 20° C. protected from light and under constant, gentle agitation. This algal suspension was mixed by repeated inversion of the vial, and centrifuged at 400 g for 10 minutes. The bright blue supernatant was transferred into the top chamber of a Millipore ultra filtration device and centrifuged for 10 minutes at 2400 rpm. The filtrate was stored in a cold and dark environment, and used within the same day of preparation. The ultra filtration devices used here have a molecular weight cut-off, such that, depending on the filtration device used, only components smaller than 3 kDa, 5 kDa, 10 KDa 30 kDa, 50 kDa, or 100 kDa will pass through the filter. A fraction, termed 1117 was produced by extracting AFA with either water or saline and isolating the components of this extract that had a molecular weight of less than 50 kDa by filtering the extract through a ultra filtration device with a 50 kDa molecular weight cut-off. This faction was tested using absorption at 620 nm, and it was determined that the concentration of phycocyanin was less than 1 mg/L.

FIG. 1 illustrates the comparative light absorbance between 300 and 750 nm of the crude AFA extract (top) and 1117 fraction (bottom). In the absorbance spectrum of the crude AFA extract, the peak at 620 nm reflects the presence of Phycocyanin. This phycocyanin peak is absent from the 1117 fraction spectrum. The peak between 300 and 350 nm indicates non-specific protein absorbance of UV light below 400 nm, and does not refer to any single compound.

The isolation of the 1117 fraction was replicated using greater quantities of starting material. Ten liters of homogenized, liquid algal biomass was centrifuged at a feed rate of 4 liters/minute in an ALFA LAVAL™ centrifuge, which separates solids from liquids. The "G" Force of the ALFA LAVAL™ centrifuge used was 6080.6 g units with a feed rate of 4 liters per minute. However, other centrifuges can be used, such as a large WESTFALIA™ centrifuge that delivers 9104 "G"s and a feed rate of 40 liters per minute.

The yellow filtrate from the ALFA LAVAL™ centrifuge was collected immediately frozen at −21° C. Subsequently, the liquid was thawed in order to concentrate the compounds by removing water. The concentrated compounds were then stored cold and dark, and either frozen or dried within the same day of preparation.

Example 2

The 1117 Fraction from AFA Contains Compounds able to Inhibit the Enzymatic Activity of Lipoxygenase These results demonstrate that a low-molecular weight fraction of AFA can be used to inhibit the enzymatic function of lipoxygenase.

Figure 2:
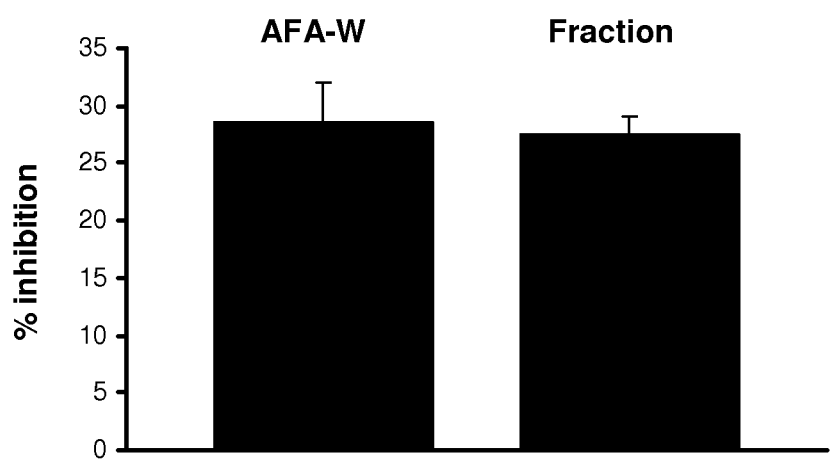
FIG. 2 is a graph showing the ability of the 1117 fraction to inhibit enzymatic activity of Lipoxygenase.

A lipoxygenase inhibitor screening kit was obtained from Cayman Chemical, and used according to the guidelines of the manufacturer. In this assay, a purified 15-Lipoxygenase enzyme from soybean was mixed with the substrate arachidonic acid in the absence versus presence of the 1117 fraction. Inhibition of lipoxygenase was also compared using a crude, unfractionated, AFA water extract. The hydroxyperoxides that are produced as a result of the lipoxygenase reaction were measured by absorbance following color development. As shown in FIG. 2, the 1117 fraction inhibited lipoxygenase as effectively as a crude water extract of AFA, indicating that the 1117 fraction retains the lipoxygenase inhibiting properties of the crude extract.

Example 3

The 1117 Fraction from AFA Contains Compounds Able to Inhibit the Formation of Reactive Oxygen Species (ROS) by Human PMN Cells These results document that AFA contains a water-soluble compound that specifically reduces ROS formation by human PMN cells.

PMN cells were isolated by applying heparinized peripheral venous blood on top of a double-gradient of 3 mL Histopaque 1119 and 3 mL of Histopaque1077. This was centrifuged for 25 minutes at 2400 rpm. The plasma and PBMC was removed, and the PMN fraction harvested. The PMN cells were washed twice in phosphate-buffered saline without calcium or magnesium, and resuspended in RPMI 1640. Serial dilutions of a 1:1 starting dilution of the 1117 fraction were added to PMN cells and cells were incubated for 20 minutes. Cells were washed twice to remove Fraction 1117, and the precursor dye DCF-DA was added. The PMN cells were incubated with DCF-DA for 1 hour, after which time unabsorbed DCF-DA was removed by two washes. Oxidative burst was then induced, either by adding $H_2O_2$ or by adding the bacterial peptide f-MLP for 45 minutes. Cells were washed, resuspended in RPMI 1640, and kept on ice until samples were acquired by flow cytometry. Oxidative damage, such as that which occurs during a reactive oxidative burst in PMN cells, transforms the DCF-DA precursor dye into a fluorescent dye. The fluorescence intensity of the cells is a measure of the intensity of the oxidative burst.

Figure 3:
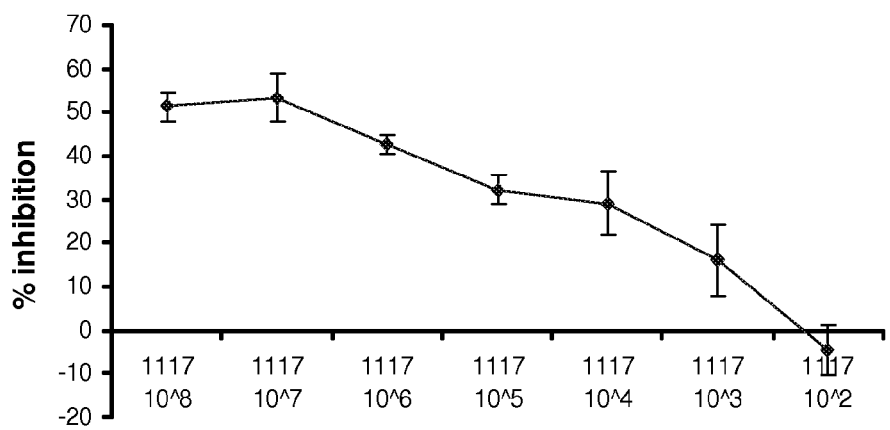
FIG. 3 is a graph showing the ability of the 1117 fraction to inhibit formation of Reactive Oxygen Species (ROS) in human PMN cells.
Figure 3:
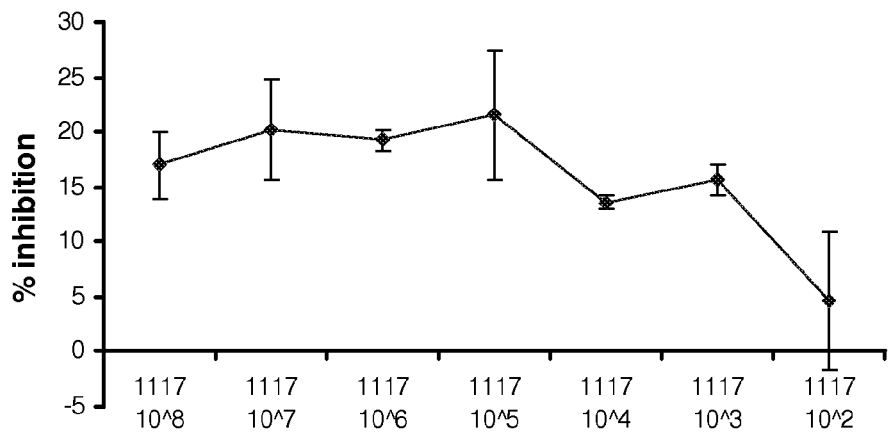

FIG. 3 shows the concentration dependent ability of 1117 fraction to inhibit ROS in PMN cells. Inhibition of background (top panel) and induced (bottom panel) ROS is shown.

Example 4

Anti-inflammatory Effect of the 1117 Fraction in Vitro-inhibition of PMN Cell Migration Towards the Inflammatory Mediator Leukotriene B4

The migration of polymorphonuclear (PMN) cells was tested using dual chamber 96-well migration plates. PMN cells are plated in the top chambers and different chemotactic agents can be added to the bottom chamber. A filter separates the two chambers, and 3 micron pores allow migration of cells from top to bottom chamber. This in vitro assay is designed to mimic the migration of inflammatory cells from blood (top chamber) into tissue (bottom chamber), with inflammatory mediators as chemoattractants.

Figure 4:
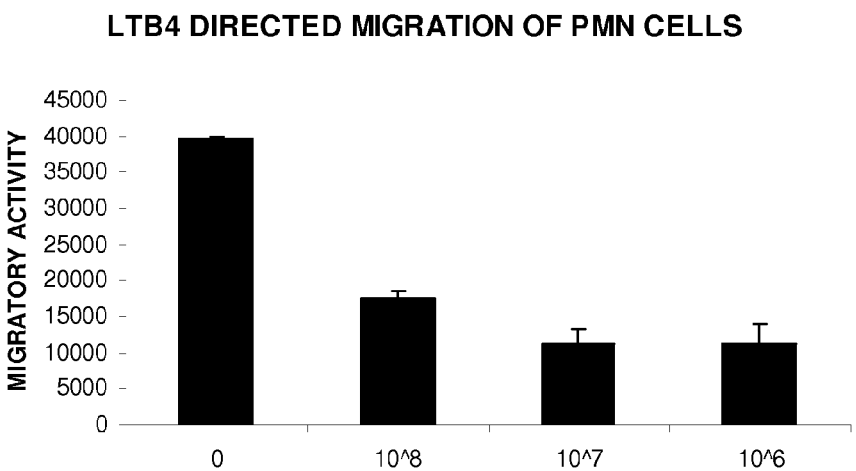
FIG. 4 is a graph showing the ability of the 1117 fraction to inhibit the directed migration of PMN cells towards the inflammatory chemoattractant Leukotriene B4.

PMN cells were plated in the top chambers with and without the 1117 fraction, and the inflammatory chemo-attractant Leukotriene B4 (LTB4) was present in the bottom chambers. Control wells included cells un-exposed to the 1117 fraction and without chemoattractant in the bottom wells. The directed migration of PMN cells resulted in measurable amounts of PMN cells in the bottom chambers. The relative amount of cells was determined by staining of the cells in the bottom chambers using the CyQuant fluorescent probe. When the 1117 fraction was added to PMN cells in the top chambers, the migration of the PMN cells towards LTB4 in the bottom chambers was reduced, even at the low dose of the 1117 fraction of 1 ng/mL (FIG. 4).

Example 5

Immuno-modulatory Effect of the 1117 Fraction: Activation of NK Cells

Figure 5:
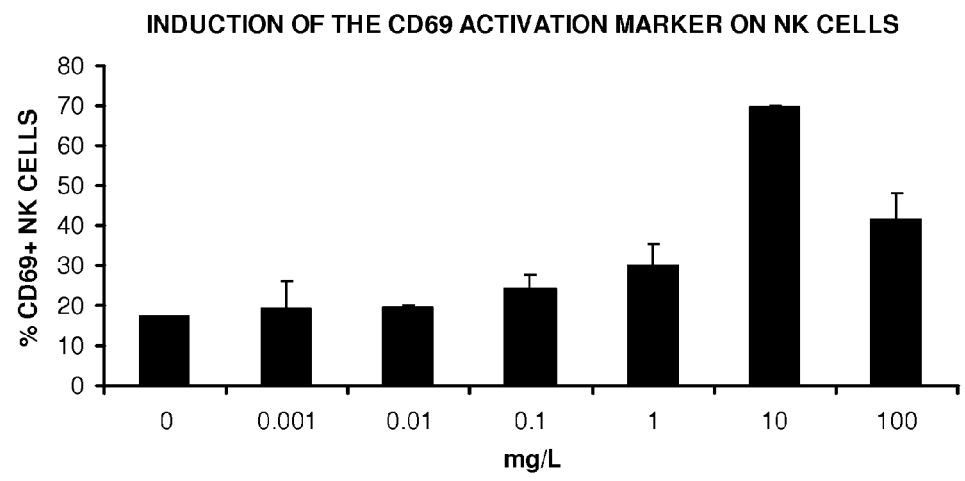
FIG. 5 is a graph showing the ability of the 1117 fraction to activate human NK cells.

The ability of the 1117 fraction to activate natural killer (NK) cells in vitro was tested. Freshly purified human peripheral blood mononuclear cells (PBMCs) were used for these assays. Peripheral venous blood samples were obtained from healthy human volunteers between the ages of 20 and 60 years. Heparinized whole blood was layered onto Histopaque 1077 and centrifuged for 25 minutes at 400 g. The PBMC-rich interface was harvested and washed twice in phosphate buffered saline. The freshly purified PBMCs were resuspended in culture medium and exposed to the 1117 fraction. The cells were plated in 96-well micro-assay plates in triplicate. Negative control wells in triplicate were left untreated, in order to have the reference value of CD69 levels without test products. After 18 hours of culture, cells were stained for the activation molecule CD69 on the surface of CD3-negative, CD56-positive NK cells using antibodies that specifically bind CD69, CD3 and CD56. The analysis (shown in FIG. 5) measured the fluorescence intensity of cells labeled for CD69 with a fluorescence-conjugated monoclonal antibody, and allowed determination if the compounds in a test product directly activated NK cells in vitro. The cells were washed in phosphate buffered saline (PBS) containing 1% bovine serum albumin and 0.02% sodium azide. Cells were resuspended in 50 µl buffer. Monoclonal antibodies were added and incubated in the dark at room temperature for 10 minutes. An additional 110 µl of buffer was added to each well, and the plates were washed. Supernatant was discarded, and the cells were resuspended in 50 µl of buffer and transferred to 0.4 mL of 1% formalin. Samples were stored dark and acquired by flow cytometry within 4 hours. Acquisition was performed using FACSCALIBUR™ flow cytometer and CELL-QUEST™ software. Analysis of fluorescence intensity of each marker was performed by electronic gating on CD3−CD56+ NK cells as well as on CD3+CD56+ NKT cells, using FLOWJOT™ software.

Example 6

Figure 6:
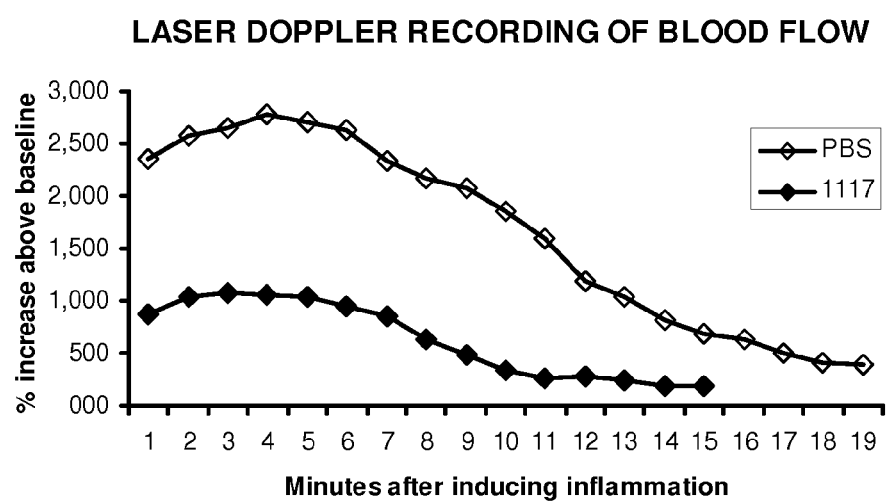
FIG. 6 is a graph showing the effect of the 1117 fraction on histamine-induced microvascular blood flow.

Anti-inflammatory Effect of the 1117 Fraction in Vivo-inhibition of the Histamine-induced Inflammatory Cascade in a Skin Model The ability of the 1117 fraction to inhibit the inflammatory cascade in response to histamine was tested. The measurement of the overall result/magnitude of the inflammatory response was measured by the increase in blood flow over a certain area and is shown in FIG. 6.

The testing was performed in a similar fashion to allergy skin testing, except that less histamine was necessary to provoke a measurable response. Where allergy testing relies on a visual inspection of swelling and redness, we used the sensitive laser Doppler to measure changes in blood perfusion. The laser Doppler measurement of perfusion measures a summary of blood perfusion in the microvasculature.

Each test subject was seated comfortably and a laser Doppler probe was attached to each forearm. The attachment was done using double-sided tape, with a hole that precisely matches the head of the probe. This allows careful detachment and re-attachment of the probe without triggering an increase in blood perfusion. An initial baseline reading was performed to record the blood flow under each Doppler probe before triggering an inflammatory response. Each probe was carefully removed, and an inflammatory reaction was provoked: Ten µL of 1:50 diluted histamine (0.2 mg/mL) was allowed to sit on the skin for 1 minute. A Hollister-Stier Prick Lancetter was used to scratch the outer layers of skin to initiate an inflammatory response. The histamine was removed carefully using a cotton tip without rubbing, 10 µL of either saline or the 1117 fraction was applied to each probe area, and was allowed to sit for 1 minute before removal. The probes were gently reapplied, and monitoring of blood perfusion was measured for 15 minutes. Analysis was performed by comparing the increase in blood perfusion to baseline over 1-minute intervals. Where the application of saline indicates the magnitude of the inflammatory response in the absence of an anti-inflammatory compound, the application of the 1117 fraction resulted in a much reduced inflammatory reaction (FIG. 6).

Example 7

Anti-inflammatory Effect of the 1117 Fraction in Vivo

The anti-inflammatory effect of the 1117 fraction is evidenced by the following:
1. A 55-year old white male experienced moderate to severe muscle pain after exercising. The person was in otherwise good health, but would consume four Advil after playing tennis. Daily consumption of 250 mg of the 1117 fraction led to complete resolution of sports-induced muscle pain after exercise within one week.
2. A 47 year old female in good health and with regular menstruation typically experienced a day during menstruation with moderate to severe menstrual cramps. On one occasion, the painful cramps were so severe that they were not relieved by 1 hour heat or 1000 mg Tylenol. A single dose of 3 mL crude liquid low molecular weight extract relieved severe menstrual cramps and intense pain. The relief happened within 5-10 minutes after consumption, and lasted 8 hours.
3. A 50 year old female in good health experienced severe, throbbing muscle pain after a 1-hour session of deep tissue massage. The pain was relieved within 30 minutes after consuming a single dose of 500 mg the 1117 fraction.

It will be apparent that the precise details of the methods or compositions described may be varied or modified without departing from the spirit of the described invention. We claim all such modifications and variations that fall within the scope and spirit of the claims below.

The invention claimed is:

1. A method of reducing inflammation in a subject, comprising:
administering to a subject with inflammation a therapeutically effective amount of a composition comprising an isolated fraction of an extract of a species of *Spirulina*, or a dried form of the isolated fraction, wherein the isolated fraction has a molecular weight distribution wherein at least 95% of the molecules in the isolated fraction are less than a cut-off weight and the cut-off weight is not more than about 50 kDa; and wherein the isolated fraction and the composition are substantially free of phycocyanin;
thereby reducing inflammation in the subject.

2. The method of claim 1, wherein the isolated fraction and the composition comprise less than about 5 mg/L phycocyanin.

3. The method of claim 1, wherein the composition comprises a pharmaceutically acceptable carrier.

4. The method of claim 1, wherein the composition is administered topically, systemically, or orally.

5. The method of claim 1, wherein the subject has an allergic reaction, inflammatory arthritis, muscle pain, asthma, or is immunosuppressed.

6. The method of claim 1, wherein the subject has an inflammation of skin, joints, muscles, digestive system, mucosal membranes, nervous system, lymph system, cardiovascular system, or endocrine system, or a combination thereof.

7. The method of claim 1, further comprising administering one or more steroidal or non-steroidal anti-inflammatory agents.

8. The method of claim 1, wherein the subject has an inflammation of a muscle and the composition comprises an isolated fraction of an extract of a species of *Spirulina*.

9. The method of claim 1, wherein reducing inflammation comprises reducing cytokine secretion.

10. The method of claim 1, wherein reducing inflammation comprises reducing enzymatic activity of lipoxygenase.

11. The method of claim 1, wherein reducing inflammation comprises reducing production of reactive oxygen species by polymorphonuclear cells.

12. The method of claim 1, wherein reducing inflammation comprises reducing polymorphonuclear cell migration.

13. The method of claim 1, wherein the cut-off weight is not more than about 3 kDa.

14. The method of claim 13, the cut-off weight is not more than about 3 kDa.

15. A method of reducing inflammation a subject, comprising:
selecting a subject with inflammation of a muscle, and
administering to a subject with inflammation a therapeutically effective amount of a composition comprising an isolated fraction of an extract of a species of *Spirulina*, or a dried form of the isolated fraction, wherein the isolated fraction has a molecular weight distribution wherein at least 95% of the molecules in the isolated fraction are less than a cut-off weight and the cut-off weight is not more than about 50 kDa; and wherein the isolated fraction and the composition are substantially free of phycocyanin;
thereby reducing the inflammation of the muscle in the subject.

16. The method of claim 15, wherein the cut-off weight is not more than about 3 kDa.

* * * * *